US011433200B2

(12) United States Patent
Lee

(10) Patent No.: US 11,433,200 B2
(45) Date of Patent: Sep. 6, 2022

(54) MECHANICAL IN-EXSUFFLATION

(71) Applicant: KONINKLIJKE PHILIPS N.V., Eindhoven (NL)

(72) Inventor: Seunghyun Lee, Spring Hill, FL (US)

(73) Assignee: Koninklijke Philips N.V., Eindhoven (NL)

(*) Notice: Subject to any disclaimer, the term of this patent is extended or adjusted under 35 U.S.C. 154(b) by 357 days.

(21) Appl. No.: 15/754,643

(22) PCT Filed: Aug. 26, 2016

(86) PCT No.: PCT/EP2016/070209
§ 371 (c)(1),
(2) Date: Feb. 23, 2018

(87) PCT Pub. No.: WO2017/032882
PCT Pub. Date: Mar. 2, 2017

(65) Prior Publication Data
US 2018/0243521 A1    Aug. 30, 2018

Related U.S. Application Data

(60) Provisional application No. 62/210,111, filed on Aug. 26, 2015.

(30) Foreign Application Priority Data

Oct. 2, 2015    (EP) .................................. 15188078

(51) Int. Cl.
*A61M 16/00* (2006.01)
*G16H 40/63* (2018.01)
(Continued)

(52) U.S. Cl.
CPC .......... *A61M 16/024* (2017.08); *A61B 5/0823* (2013.01); *A61M 16/0051* (2013.01);
(Continued)

(58) Field of Classification Search
CPC ..... A61M 16/021-026; A61M 16/0066-0081; A61M 16/0051;
(Continued)

(56) References Cited

U.S. PATENT DOCUMENTS 5,277,196 A * 1/1994 Hankinson ............. A61B 5/087
600/537
8,985,112 B2    3/2015 Ikei
(Continued)

FOREIGN PATENT DOCUMENTS

JP    2007105161 A * 4/2007 ............... A61B 5/08

OTHER PUBLICATIONS

Merriam-Webster, Definition of Initiate, Accessed Oct. 22, 2021, https://www.merriam-webster.com/dictionary/initiate (Year: 2021).*

*Primary Examiner* — Elliot S Ruddie
(74) *Attorney, Agent, or Firm* — Daniel H. Brean

(57) ABSTRACT

The present disclosure pertains to a method and system configured for cough synchronization in a mechanical insufflation-exsufflation system. The system is configured to synchronize (712) the transition from an insufflation mode to an exsufflation mode to a patient initiated cough by detecting cough effort of the patient e.g. at the end of the insufflation phase. The detection of cough effort of the patient is based on one or more parameters associated with gas in the system. Upon detecting that the patient is initiating a cough, the system automatically switches the insufflation mode to the exsufflation mode to assist the patient to generate an effective cough.

14 Claims, 8 Drawing Sheets

(51) Int. Cl.
    *A61B 5/08*     (2006.01)
    *A61M 16/10*     (2006.01)
    *G16H 20/40*     (2018.01)

(52) U.S. Cl.
CPC ........ *A61M 16/0069* (2014.02); *G16H 40/63* (2018.01); *A61M 16/0057* (2013.01); *A61M 16/0066* (2013.01); *A61M 16/0072* (2013.01); *A61M 16/0075* (2013.01); *A61M 2016/003* (2013.01); *A61M 2016/0015* (2013.01); *A61M 2016/0027* (2013.01); *A61M 2016/0036* (2013.01); *A61M 2016/102* (2013.01); *A61M 2205/332* (2013.01); *A61M 2205/3368* (2013.01); *A61M 2205/35* (2013.01); *A61M 2205/3553* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2230/40* (2013.01); *A61M 2230/42* (2013.01); *A61M 2230/43* (2013.01); *A61M 2230/50* (2013.01); *G16H 20/40* (2018.01)

(58) Field of Classification Search
CPC ...... A61M 16/0057; A61M 2016/0015; A61M 2016/0018; A61M 2016/0024; A61M 2016/0027; A61M 2016/003–0042; A61M 2016/102; A61M 2205/332; A61M 2205/3368; A61M 2205/35; A61M 2205/3553; A61M 2205/3561; A61M 2205/3584; A61M 2205/3592; A61M 2205/50; A61M 2205/502; A61M 2230/40–50; G16H 20/40; G16H 40/60–63; A61B 5/08; A61B 5/0823
USPC ..................................................... 128/205.19
See application file for complete search history.

(56) References Cited

U.S. PATENT DOCUMENTS

| | | | |
|---|---|---|---|
| 2004/0267150 A1* | 12/2004 | Lomask | A61B 5/0823 600/529 |
| 2007/0186928 A1 | 8/2007 | Be eri | |
| 2007/0199566 A1* | 8/2007 | Be'eri | A61M 16/0051 128/204.23 |
| 2011/0220107 A1 | 9/2011 | Kimm | |
| 2012/0111329 A1 | 5/2012 | Brand | |
| 2013/0269698 A1 | 10/2013 | Balko | |
| 2014/0150791 A1* | 6/2014 | Birnkrant | A61M 16/024 128/204.23 |
| 2014/0373844 A1* | 12/2014 | Brand | A61M 16/024 128/204.22 |
| 2015/0231348 A1 | 8/2015 | Lee | |
| 2016/0310068 A1* | 10/2016 | Haviv | A61B 5/4836 |
| 2017/0325735 A1* | 11/2017 | Brand | A61M 16/024 |

* cited by examiner

MECHANICAL IN-EXSUFFLATION

CROSS-REFERENCE TO RELATED APPLICATIONS

This patent application claims the priority benefit under 35 U.S.C. § 371 of international patent application no. PCT/EP2016/0707209, filed Aug. 26, 2016, which claims the benefit of European Patent Application No. 15188078.8, filed on Oct. J2, 2015, and also claims the priority benefit under 35 U.S.C. § 119(e) of U.S. Provisional Application No. 62/210,111, filed on Aug. 26, 2015, the contents of each of which are herein incorporated by reference.

FIELD OF THE INVENTION

The present disclosure pertains to a mechanical insufflation-exsufflation configured to synchronize a patient-initiated cough with a transition from an insufflation cycle to an exsufflation cycle.

BACKGROUND OF THE INVENTION

US 2007/0199566 discloses a respiratory device that can perform mechanical ventilation and/or inexsufflation. The respiratory device can include a mechanical medical ventilator, a sensor, a display and a processor. The mechanical medical ventilator assists a patient with the respiratory cycle. The sensor can measure an intra-thoracic respiratory parameter during the respiratory cycle. The display can display a graphical representation that dynamically depicts at least one of a patient's lung or thorax based on the intra-thoracic respiratory parameter in real-time during the respiratory cycle. The processor can update the graphical representation on the display in real-time based on the respiratory parameter. The processor updates the graphical representation to depict at least one of an expansion or a contraction of at least one of the lung or thorax during the respiratory cycle. Inexsufflators are used to simulate a natural cough to remove secretions in the patient's lungs and air passages.

US 2011/0220107 discloses a system and method of insufflating-exsufflating a subject that enables monitoring and/or control over an enhanced set of breathing parameters during insufflation/exsufflation. The system and/or method may include automatic triggering and/or notification to a caregiver of insufflation-exsufflation. The insufflation-exsufflation of the subject may be preceded by a secretion loosing routine that loosens secretions in the airway of the subject without moving the loosened secretions up the airway.

US 2012/0111329 discloses a device for assisting a cough, based on an oscillation pressure. The oscillation pressure causes a periodic oscillation airflow in a lung system and the periodic oscillation airflow comprises an oscillation exhalation airflow and an oscillation inhalation airflow. The device comprises a controlling unit, and the controlling unit comprises: a first determining unit for determining whether an inhalation of the lung system is complete, so as to control a valve which is to be closed for isolating the lung system from the external environment, a second determining unit for determining whether an internal air pressure in the lung system is larger than a pre-defined pressure threshold, and a detecting unit for detecting the start of the oscillation exhalation airflow, so as to control the valve which is to be opened for starting a cough.

A mechanical in-exsufflator (M I-E) is a vital tool for invasive and non-invasive secretion management in pulmonary critical and/or re-habitational environments. In order to improve M I-E therapy efficacy and patient comfort, clinicians instruct the patient, who has intact cough reflex response, to actively cough as the M I-E device switches from the insufflation phase to the exsufflation phase. The primary method to synchronize the patient's cough effort with the transition of the M I-E device is a verbal instruction, where the clinicians instruct the patient to cough immediately before the M I-E device is ready to switch from the insufflation phase to the exsufflation phase. Some patients struggle to follow the verbal instruction to synchronize the cough due to the slow and/or varying reflex of the laryngeal maneuver required to generate an effective cough.

There is no effective way currently to synchronize the patient's cough effort with the transition of the M I-E device from the insufflation phase to the exsufflation phase. Most clinicians relay on the patient's ability to follow a verbal command to cough, which often leads to a little or no success. Some M I-E device offers an auditable beep before switching to the exsufflation phase; however, feedbacks from the clinicians indicate that such audible beep is ineffective due to the patient's inability to coordinate the laryngeal maneuver to the audible beep.

SUMMARY OF THE INVENTION

Therefore, there is a need to provide an improved solution to help the patients to cough immediately when the M I-E device switches from the insufflation phase to the exsufflation phase. The invention is defined by the independent claims. The dependent claims define advantageous embodiments.

The present disclosure relates to a method and system that dynamically synchronizes a patient's cough with the transition of an M I-E device from the insufflation phase to the exsufflation phase by monitoring the patient's cough effort e.g. during and/or after the insufflation phase. In addition to the capability of operating between the insufflation phase and the exsufflation phase in accordance with a fixed interval configuration, a cough synchronization mode is provided to automatically switch the M I-E device from the insufflation phase to the exsufflation phase once the patient's cough effort is detected. The cough triggering based exsufflation of the present invention improves the patient comfort and therapy effectiveness due to improved synchronicity.

Accordingly, one or more aspects of the present disclosure relate to a system configured for cough synchronization. The system comprises a pressure generator, a subject interface, one or more sensors, and one or more processors. The pressure generator is configured to generate a pressurized flow of breathable gas for delivery to an airway of the subject, the pressure generator configured to operate in an insufflation mode and an exsufflation mode. The subject interface is configured to place the pressure generator in fluid communication with the airway of the subject. The one or more sensors are operatively coupled to the subject interface and configured to generate one or more output signals related to one or more parameters associated with the gas in the subject interface. The one or more processors are operatively connected to the one or more sensors to receive the output signals and configured by machine-readable instructions to compare the one or more parameters associated with the gas in the subject interface with one or more reference values that indicate cough effort by the subject; determine an initiation of a cough by the subject based on the comparison; synchronize a transition of the pressure generator from the insufflation mode to the exsufflation mode with the initiation of the cough by the subject; and control the pressure generator to generate the pressurized flow of breathable gas for delivery to the airway to exsufflate the subject.

Another aspect of the present disclosure relates to a method for cough synchronization in a system. The system comprises a pressure generator, a subject interface, one or more sensors, and one or more processors. The processor comprises a control component, a parameter analysis component, a decision component and a synchronization component. The method comprises generating a pressurized flow of breathable gas for delivery to an airway of the subject with the pressure generator, the pressure generator configured to operate in an insufflation mode and an exsufflation mode; communicating the pressurized flow of breathable gas to the airway of the subject with the subject interface; generating output signals related to one or more parameters associated with gas in the subject interface with the one or more sensors; receiving the output signals with the one or more processors; executing machine-readable instructions with the one or more processors, wherein the machine-readable instructions comprise comparing the one or more parameters associated with the gas in the subject interface with one or more reference values that indicate cough effort by the subject; determining an initiation of a cough by the subject based on the comparison; synchronizing a transition of the pressure generator from the insufflation mode to the exsufflation mode with the initiation of the cough by the subject; and controlling the pressure generator to generate the pressurized flow of breathable gas for delivery to the airway to exsufflate the subject.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
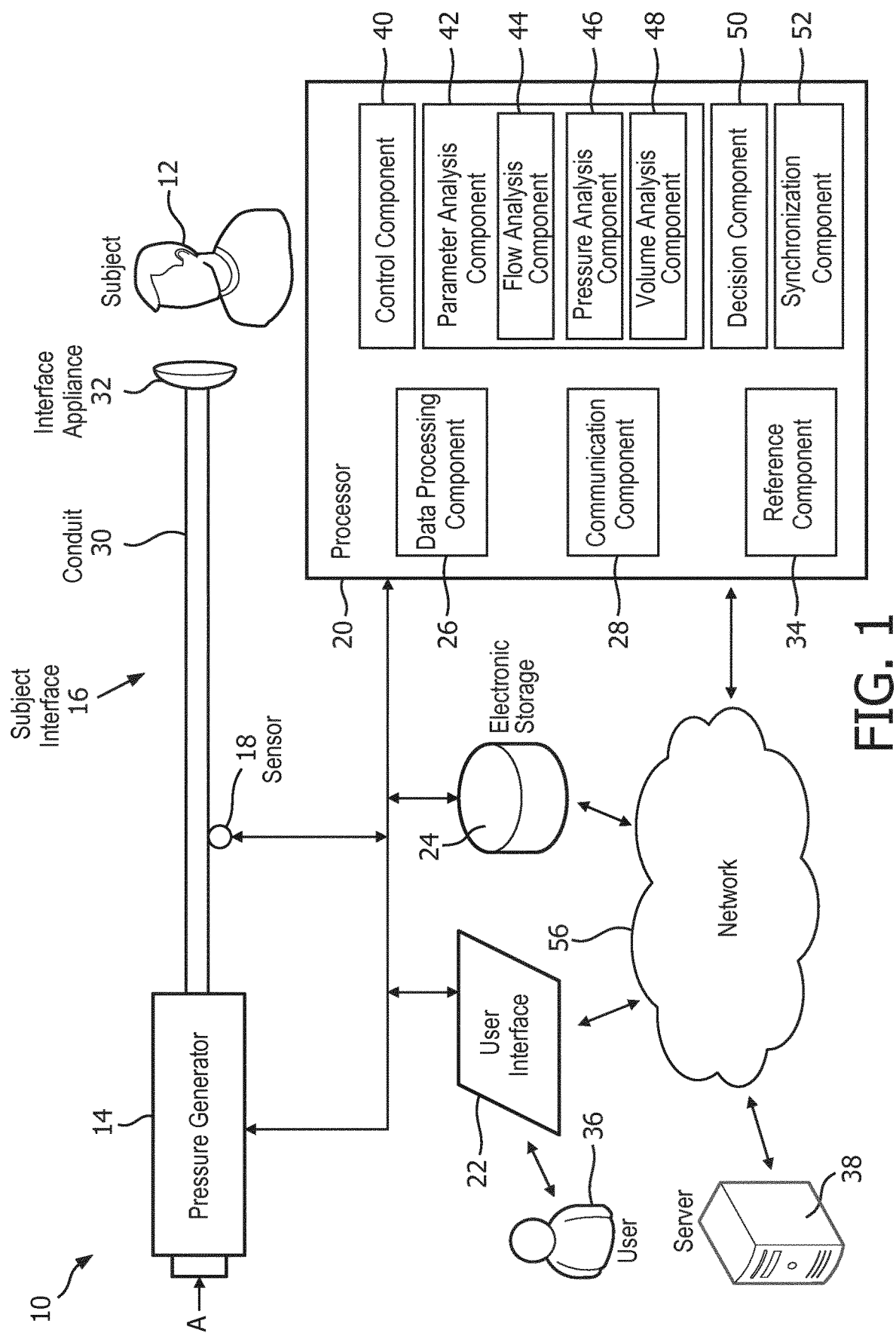
FIG. 1 illustrates an exemplary embodiment of a system configured to synchronize a cough of a subject with an M I-E exsufflation cycle.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs.

As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates an exemplary embodiment of system 10 configured to synchronize a cough of a subject with an M I-E exsufflation cycle. In some embodiments, system 10 comprises a pressure generator 14, a subject interface 16, one or more sensors 18, one or more processors 20, a user interface 22, one or more electronic storages 24, and/or other components. System 10 is configured to monitor the gas in subject interface 16 communicated to the airway of subject 12, and determine whether subject 12 is attempting to cough. System 10 is further configured to automatically switch from the insufflation mode to the exsufflation mode upon determining a cough effort of subject 12 to exsufflate subject 12. System 10 is configured to dynamically control the cough synchronization in one or more therapy cycles with no need to manually configure and/or re-configure general settings of the pressurized flow such as, for example, pressure amplitudes, a frequency range, and/or other parameters of the pressure waveform.

Pressure generator 14 is configured to operate in an insufflation mode and an exsufflation mode. In the insufflation mode, pressure generator 14 generates a positive pressurized flow of breathable gas to deliver to the airway of subject 12, i.e., inflow to subject 12. In the exsufflation mode, pressure generator 14 generates a negative pressurized flow of breathable gas to draw gas from the airway of subject 12, i.e., outflow from subject 12. In some embodiments, the duration for each of the insufflation phase and the exsufflation phase may be configured in accordance with the inexsufflation therapy requirement. For example, the durations for the insufflation phase and the exsufflation phase may be configured to be a same time period. In some embodiments, the insufflation phase may be maintained for an arbitrary duration until a cough effort of subject 12 is determined, which automatically triggers a transition to an exsufflation phase. Pressure generator 14 may be configured such that one or more parameters associated with the pressurized flow of breathable gas in addition to and/or other than pressure are adjustable. The one or more parameters may include, for example, one or more of volume, flow rate, temperature, gas composition, velocity, acceleration, and/or other parameters.

Pressure generator 14 receives a gas flow from a gas source, such as but not limited to the ambient atmosphere (indicated by an arrow A in FIG. 1) and elevates the pressure of the received gas flow for delivery to the airway of subject 12. Pressure generator 14 may include any device that is capable of elevating the pressure of the received gas flow for delivery to the airway of subject 12, for example, a pump, blower, piston, or bellows. In some embodiments, pressure generator 14 may further include one or more valves for controlling the pressure, flow rate, flow direction, oscillation frequency, and/or other parameters associated with the received gas flow. The present disclosure contemplates controlling the operating speed of the blower, for example, either alone or in combination with the one or more valves and/or other devices contained in and/or external to pressure generator 14, in order to control the pressure and/or flow of gas provided to subject 12. For example, pressure generator 14 may control the pressure direction of the flow of gas to be positive during the insufflation phase such that the gas is delivered to the airway of subject 12, and control the pressure direction of the flow of gas to be negative during the exsufflation phase such that the gas is drew from the airway of subject 12.

Pressure generator 14 may control the pressure level of the flow of gas at a first pressure level during the insufflation phase. The first pressure level is set such that the lungs of subject 12 are at least partially filled during insufflation. At the end of the insufflation phase, pressure generator 14 reduces the pressure level of the flow of gas and switches to the exsufflation phase. Pressure generator 14 may control the pressure level of the flow of gas at a second pressure level during the exsufflation phase. The second pressure level is lower than the first pressure level, and the abruptness of the pressure decrease from the first pressure level to the second pressure level is sufficient to remove mucus and/or other debris from the airway and/or lungs of subject 12. The second pressure level may be a negative pressure below an atmospheric pressure. Pressure generator 14 may return to zero pressure phase, i.e., pause mode, after the exsufflation phase, and reset the pressure level of the flow of gas to the first pressure level to prepare for another inexsufflation therapy. Pressure generator 14 may perform one or more cycles of inexsufflation in accordance with the therapy requirement. In some embodiments, pressure generator 14 is a device dedicated to inexsufflation. In some embodiments, pressure generator 14 is a ventilator and/or positive airway pressure device configured to provide therapy other than and/or in addition to inexsufflation.

Subject interface 16 is configured to interface with the airway of subject 12 and provide fluid communication between pressure generator 14 and the airway of subject 12. In some embodiments, subject interface 16 comprises a conduit 30, an interface appliance 32, and/or other components. Conduit 30 is configured to form a transmission path for the pressurized flow of breathable gas to be delivered to interface appliance 32. Interface appliance 32 is configured to deliver the received gas to the airway of subject 12. Conduit 30 may be a flexible length of hose, or other conduit, that places interface appliance 32 in fluid communication with pressure generator 14. Interface appliance 32 may be removably coupled to conduit 30 and/or other conduits and/or other interface appliances used to deliver respiratory therapy to subject 12. In some embodiments, interface appliance 32 is non-invasive. As such, interface appliance 32 non-invasively engages subject 12. Non-invasive engagement includes removably engaging an area (or areas) surrounding one or more external orifices of the airway of subject 12 (e.g., nostrils and/or mouth) to communicate gas between the airway of subject 12 and subject interface 16. Some examples of non-invasive interface appliance 32 may include a blow tube, a nasal cannula, a nasal mask, a nasal/oral mask, a full face mask, a total face mask, or other interface appliances that communicate a flow of gas with an airway of a subject. In some embodiments, interface appliance 32 is invasive. Some examples of invasive interface appliance 32 may include endotracheal tubes, tracheostomy tubes, and/or other devices. The present disclosure is not limited to these examples, and contemplates delivery of the flow of gas to the subject using any interface appliance.

Although subject interface 16 is illustrated in FIG. 1 as a single-limbed interface for the delivery of the pressurized flow of gas to the airway of subject 12, this is not intended to be limiting. The scope of the present disclosure comprises double-limbed configuration, where one of the double-limbed configuration provides the pressurized flow of gas to the airway of the subject and another of the double-limbed configuration exhausts gas from the subject.

Sensors 18 are configured to generate output signals related to one or more parameters associated with gas in subject interface 16. Sensors 18 are operatively coupled to subject interface 16 to collect data related to the real-time measurements of the one or more parameters. The one or more parameters may comprise flow rate, pressure, volume, temperature, humidity, velocity, and/or other gas parameters. Sensors 18 may be configured with an integrated sensing function to collect the real-time measurements for the one or more parameters. In some embodiments, sensors 18 may comprise one or more sensors, each of which performs a sensing function directed to a specified parameter. Sensors 18 may generate output signals related to the real-time measurements of the one or more parameters associated with gas in subject interface 16 based on an operating parameter of the pressure generator 14 (e.g., a motor current, voltage, rotational velocity, and/or other operating parameters), but the present disclosure is not intended to be limiting. Although sensors 18 are illustrated at a single location within (or in communication with) conduit 30 between interface appliance 32 and pressure generator 14, this is not intended to be limiting. Sensors 18 may include sensors disposed in a plurality of locations, such as for example, within pressure generator 14, within (or in communication with) interface appliance 32, and/or other locations. Sensors 18 may be configured with wireless communication capabilities to transmit the output signals.

Processor 20 is configured to receive the output signals from sensors 18 and process the real-time measurements related to the one or more parameters read from the output signals. Processor 20 may include one or more of a digital processor, an analog processor, a digital circuit designed to process information, an analog circuit designed to process information, a state machine, a transmitter, a receiver, and/or other mechanisms for electronically processing information. Although processor 20 is shown in FIG. 1 as a single entity, this is for illustrative purposes only. In some implementations, processor 20 includes one or more processing units. The one or more processing units may be physically located within a same device, or processor 20 may represent processing functionality of a plurality of devices operating in coordination.

As shown in FIG. 1, processor 20 may be configured to execute one or more computer programmed components. The one or more computer programmed components may comprise a control component 40, a parameter analysis component 42, a decision component 50, a synchronization component 52, a data processing component 26, a communication component 28, a reference component 34, and/or other components. The parameter analysis component 42 may further comprise a flow analysis component 44, a pressure analysis component 46, and a volume analysis component 48. Processor 20 may be configured to execute components 26, 28, 34, 40, 42, 44, 46, 48, 50 and 52 by software; hardware; firmware; some combination of software, hardware, and/or firmware; and/or other mechanisms for configuring processing capabilities on processor 20.

Each of the one or more computer programmed components comprises a set of algorithms implemented on processor 20 that instructs processor 20 to perform one or more operations related to inexsufflation therapy, cough synchronization, and/or other therapies. For example, control component 40 comprises algorithms implemented on processor 20 that instruct processor 20 to perform controlling of pressure generator 14 to generate the pressurized flow of gas. Parameter analysis component 42 comprises algorithms implemented on processor 20 that instruct processor 20 to analyze information related to real-time measurements of the one or more parameters associated with the gas in subject interface 16. Decision component 50 comprises algorithms implemented on processor 20 that instruct processor 20 to determine whether a cough is initiated by subject 12 based on one or more comparison results from the parameter analysis component 42.

Synchronization component 52 comprises algorithms implemented on processor 20 that instruct processor 20 to send a cough synchronization signal to control component 40 based on the decision signal received from decision component 50. Data processing component 26 comprises algorithms implemented on processor 20 that instruct processor 20 to receive output signals from sensors 18 and process data read out from the output signals. Communication component 28 comprises algorithms implemented on processor 20 that instruct processor 20 to perform communications within one or more components of processor 20, and between processor 20 and other components of system 10 and/or other network components. Reference component 34 comprises algorithms implemented on processor 20 that instruct processor 20 to define one or more reference values used to determine whether a cough is initiated by subject 12.

It should be appreciated that although components 26, 28, 34, 40, 42, 44, 46, 48, 50 and 52 are illustrated in FIG. 1 as being co-located within a single processing unit, in implementations in which processor 20 includes multiple processing units, one or more of these components may be located remotely from the other components. The description of the functionality provided by the different components 26, 28, 34, 40, 42, 44, 46, 48, 50 and 52 described below is for illustrative purposes, and is not intended to be limiting, as any of components 26, 28, 34, 40, 42, 44, 46, 48, 50 and 52 may provide more or less functionality than is described. For example, one or more of components 26, 28, 34, 40, 42, 44, 46, 48, 50 and 52 may be eliminated, and some or all of its functionality may be provided by other ones of components 26, 28, 34, 40, 42, 44, 46, 48, 50 and 52. As another example, processor 20 may be configured to execute one or more additional components that may perform some or all of the functionality attributed below to one of components 26, 28, 34, 40, 42, 44, 46, 48, 50 and 52.

Control component 40 is configured to control pressure generator 14 to generate the pressurized flow of gas in accordance with the inexsufflation operation mode. For example, control component 40 may determine one or more initial parameters related to the pressure waveform and instruct pressure generator 14 to generate a positive pressurized flow of gas to deliver to the airway of subject 12 to begin an inexsufflation therapy cycle. The one or more initial parameters may be determined during manufacturing, determined based on real-time input received at user interface 22, determined based on historical information related to one or more previous inexsufflation therapies received by subject 12, and/or determined by other methods.

Control component 40 is further configured to dynamically adjust one or more initial parameter 16 based on an output from decision component 50, and send an updated instruction to pressure generator 14 to generate the pressurized flow of gas accordingly. For example, if the output from decision component 50 indicates that subject 12 is attempting to cough, control component 40 instructs pressure generator 14 to adjust the level of the pressure waveform and switch to the exsufflation phase to assist subject 12 to generate an effective cough.

In some embodiments, control component 42 may control pressure generator 14 such that the pressure support provided to the subject via the flow of gas comprises therapy in addition to inexsufflation. Therapy in addition to and/or instead of inexsufflation may comprise, for example, continuous positive airway pressure support (CPAP), bi-level positive airway pressure support, proportional positive airway pressure support, and/or other types of pressure support therapy.

Parameter analysis component 42 is configured to analyze information related to real-time measurements of the one or more parameters associated with the gas in subject interface 16. As such, parameter analysis component 42 may further comprises a flow analysis component 44, a pressure analysis component 46 and a volume analysis component 48. Flow analysis component 44 is configured to compare a flow rate associated with the gas in subject interface 16 with a flow rate threshold at the end of the insufflation phase, and send the comparison result to decision component 50. In some embodiments, when it is determined that the flow rate exceeds the flow rate threshold, decision component 50 outputs a decision signal to synchronization component 52 indicating that a cough is initiated by subject 12. Pressure analysis component 46 is configured to compare a pressure level associated with the gas in subject interface 16 with a pressure level threshold at the end of the insufflation phase, and send the comparison result to decision component 50. In some embodiments, when it is determined that the pressure level exceeds the pressure level threshold, decision component 50 outputs a decision signal to synchronization component 52 indicating that a cough is initiated by subject 12. Volume component 48 is configured to compare a volume level associated with the gas in subject interface 16 with a volume level threshold at the end of the insufflation phase, and send the comparison result to decision component 50. In some embodiments, when it is determined that the volume level exceeds the volume level threshold, decision component 50 outputs a decision signal to synchronization component 52 indicating that a cough is initiated by subject 12.

In some embodiments, pressure analysis component 46 may be configured to measure the velocity of the pressure level change at the end of the insufflation phase, and compare the velocity of the pressure level change to a pressure waveform slope threshold. Once the velocity of the pressure level change exceeds the pressure waveform slope threshold, the comparison result is sent to decision component 50. In some embodiments, flow analysis component 44 may be configured to measure the velocity of the flow rate change at the end of the insufflation phase, and compare the velocity of the flow rate change to a flow rate waveform slope threshold. Once the velocity of the flow rate change exceeds the flow rate waveform slope threshold, the comparison result is sent to decision component 50. In some embodiments, flow analysis component 44 may measure the duration of an observed flow rate change at the end of the insufflation phase, and compare the duration to a time threshold.

In some embodiments, pressure analysis component 46 may measure the duration of an observed pressure level change at the end of the insufflation phase, and compare the duration to a time threshold to determine whether a cough is initiated by a subject. In some embodiments, volume analysis component 48 may measure the duration of an observed volume level change at the end of the insufflation phase, and compare the duration to a time threshold. It should be appreciated that the functionalities of flow analysis component 44, pressure analysis component 46 and volume analysis component 48 described above are for illustrative purpose, and are not intended to be limiting. Flow analysis component 44, pressure analysis component 46 and volume analysis may be configured to analyze all aspects of the flow rate, pressure level and volume level in accordance with the requirement of therapy. In some embodiments, flow analysis component 44, pressure analysis component 46 and volume analysis component 48 may be configured to continuously monitor the measurements associated with one or more parameters of gas during the entire insufflation phase, at the end of the insufflation phase, and after the insufflation phase.

The one or more parameters analyzed by parameter analysis component 42 may comprise, for example, one or more of a flow rate, pressure, a volume, humidity, temperature, acceleration, velocity, respiration rate, tidal volume, and/or other parameters. It should be appreciated that parameter analysis component 42 is not limited to comprise components 44, 46 and 48; one or more other components configured to analyze information related to the measurements of one or more other parameters associated with the gas in subject interface 16 may also be included. Although components 44, 46 and 48 are illustrated in FIG. 1 as being separate components, these components may be integrated as one function component that is capable to perform analysis over a plurality of parameters associated with the gas in subject interface 16. The description of the functionalities of components 44, 46 and 48 set forth above is for illustrative purposes, and is not intended to be limiting, as any of components 44, 46 and 48 may provide more or less functionality than is described, and may be modified and/or upgraded to include newly developed functions. It should be appreciated that whether a cough is initiated by subject 12 is not limited to be based on one sole parameter such as flow rate, pressure level, volume level, and/or other parameter associated with the gas in subject interface 16; a combination of one or more comparison results with respect to one or more parameters may be used to determine whether a cough is initiated by subject 12. For example, a decision whether a cough is initiated by subject 12 is made based on the comparison results from flow analysis component 44 and pressure analysis component 46.

Decision component 50 is configured to determine whether a cough is initiated by subject 12 based on one or more comparison results from the parameter analysis component 42. Decision component 50 may further consider one or more other parameters related to the gas in subject interface 16 to determine whether a cough is initiated by subject 12. Decision component 50 may be configured to apply one or more strategies to improve the accuracy of the determination and/or to reduce false alarm rate, which in turn, leads to an effective cough of the subject and/or improved comfort of the subject. For example, decision component 50 may assign a higher weight to the pressure level comparison than the flow rate comparison if information related to past therapies received by subject 12 indicates that subject 12 is sensitive to the pressure and has responded better with the pressure triggered cough synchronization. The one or more strategies and/or the one or more parameters that are considered by decision component 50 may be configured during manufacturing, configured based on input received at user interface 22, configured based on past therapy records associated with subject 12, and/or other factors.

Synchronization component 52 is configured to send a cough synchronization signal to control component 40 based on the decision signal received from decision component 50. For example, if the decision signal received is "1" which indicates a positive detection of a cough effort of subject 12, synchronization component 52 generates a cough synchronization signal that instructs control component 40 to control pressure generator 14 to switch immediately from the insufflation mode to the exsufflation mode. In some embodiments, if no positive decision signal is received from decision component 50, synchronization component 52 periodically communicates with control component 40 to maintain pressure generator 14 in the insufflation phase. The functionalities of synchronization component 52 described above are for illustrative purposes, and are not intended to be limiting. Synchronization component 52 may be configured to generate one or more other signals in accordance with the one or more strategies used by decision component 50 to adjust the operation of pressure generator 14 and/or other components of system 10.

Reference component 34 is configured to define one or more reference values used to determine whether a cough is initiated by subject 12. In some embodiments, the one or more reference values are measurement thresholds related to one or more parameters associated with the gas in subject interface 16. The one or more reference values may be pre-defined at manufacturing, configured with respect to a specified therapy or a specified subject, and/or other criteria that are applied to improve the therapy efficacy. In some embodiments, the one or more references may be configured by user 36 based on the analysis of historical information related to past therapies on a plurality of subjects.

Data processing component 26 is configured to receive output signals from sensors 18 and process data read out from the output signals so that reliable information is forwarded to parameter analysis component 42. Data collected from sensors 18 may sometimes comprise one or more types of noise signals from the surrounding environment and/or from other sources that affect the accuracy of information read out from the output signals. For example, a noise signal may magnify the measured pressure level at the end of insufflation phase, thus, triggering a synchronization signal which is earlier than an actual cough of subject 12. As such, a transition from the insufflation phase to the exsufflation phase draws air from the airway of subject 12 while subject 12 is not ready to cough, causing discomfort of subject 12. Data processing component 26 may be configured to filter out the added noise signals based on one or more algorithms such that data after filtering provides more accurate information related to the real-time measurements of the one or more parameters.

Communication component 28 is configured to perform communications within one or more components of processor 20, and between processor 20 and other components of system 10 and/or other network components. In some embodiments, communication component 28 communicates with server 38 remotely connected to network 56 and downloads one or more software packages from electronic storage 24 to modify and/or upgrade the functionalities of one or more components of processor 20. In some embodiments, communication component 28 communicates with electronic storage 24 locally connected to processor 20 or remotely connected to network 56 to retrieve historical information related to past therapies associated with a plurality of subjects, and provide the historical information to user 36 to determine and/or adjust one or more parameters associated with the pressurized flow of gas. The present disclosure contemplates any techniques for communication including but not limited to hard-wired and wireless communications.

Electronic storage 24 is configured to electronically stores information in an electronic storage media. Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may store software algorithms, information determined by processor 20, information received via user interface 22, and/or other information that enables system 10 to function properly.

User interface 22 is configured to provide an interface between system 10 and user 36. This enables data, results, and/or instructions and any other communicable items, collectively referred to as "information," to be communicated between user 36 and one or more of subject interface 16, processor 20, and/or other components of system 10. For example, user 36 may input a pressure level threshold for a cough synchronization therapy cycle and the inputted pressure level threshold is transmitted to processor 20 for further analysis. In some embodiments, information entered through user interface 22 to system 10 may include inexsufflation therapy initial percussive pressure waveform parameters, frequency range, an oscillating flow rate amplitude effectiveness threshold, and/or other information. Interface devices suitable for inclusion in user interface 22 include a keypad, buttons, switches, a keyboard, knobs, levers, a display screen, a touch screen, speakers, a microphone, a printer, and/or other interface devices. In some embodiments, user interface 22 includes a plurality of separate interfaces. In some embodiments, user 36 includes subject 12, a clinician, a nurse, an interested party, and/or any other entities.

Network 56 is configured to transmit information among a plurality of network components. For example, network 56 receives inputs from user 36 at user interface 22 related to the configuration of one or more parameters associated with the gas for a therapy cycle, and transmits the inputs to processor 20 for further processing. In some embodiments, a request inputted via user interface 22 is received at server 38 via network 56 to retrieve historical information related to past therapies on a plurality of subjects for analysis. Network 56 forwards an instruction from server 38 to retrieve the requested historical information related to past therapies on a plurality of subjects from electronic storage 24. Network 56 may be a single network or a combination of multiple networks. For example, network 56 may be a local area network (LAN), a wide area network (WAN), a public network, a private network, a proprietary network, a Public Telephone Switched Network (PSTN), the Internet, a wireless communication network, a virtual network, and/or any combination thereof.

Figure 2:
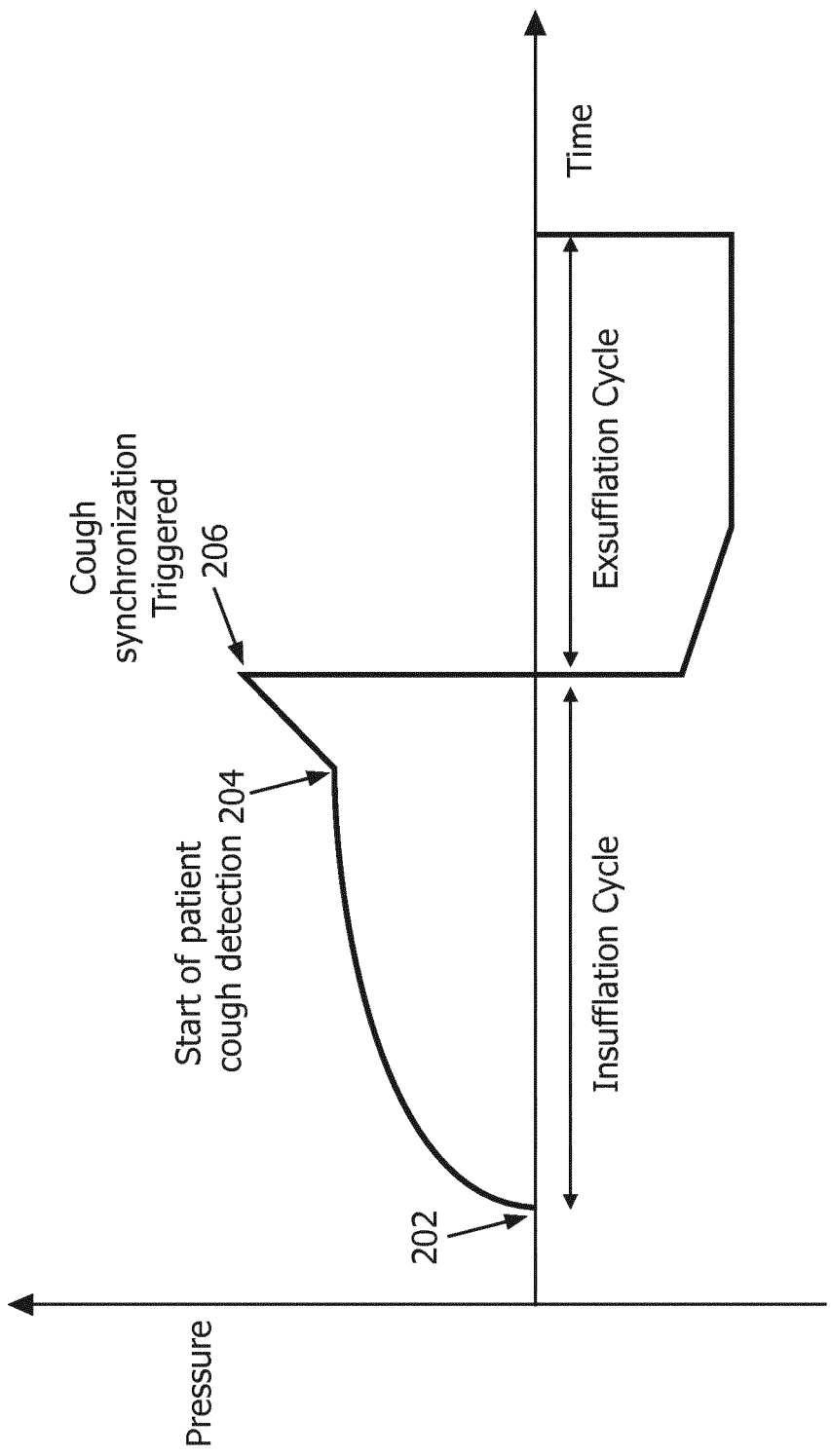
FIG. 2 illustrates an exemplary embodiment of cough synchronization based on a pressure waveform associated with breathable gas in a subject interface communicated to an airway of a subject.

FIG. 2 illustrates an exemplary embodiment of cough synchronization based on a pressure waveform associated with breathable gas in a subject interface communicated to an airway of a subject. An insufflation cycle begins at time 202. Accordingly, the pressure level associated with the gas in subject interface 16 starts to increase and reaches a plateau at the end of the insufflation cycle. If at the end of the insufflation cycle, an increase in the pressure level is observed at time 204, which may indicate a short inflow to the airway of subject 12, patient cough detection automatically starts. When the pressure level is increased to exceed a pressure level threshold at time 206, cough synchronization is triggered and pressure generator 14 in FIG. 1 automatically switches to the exsufflation cycle to assist with the patient's cough.

Figure 3:
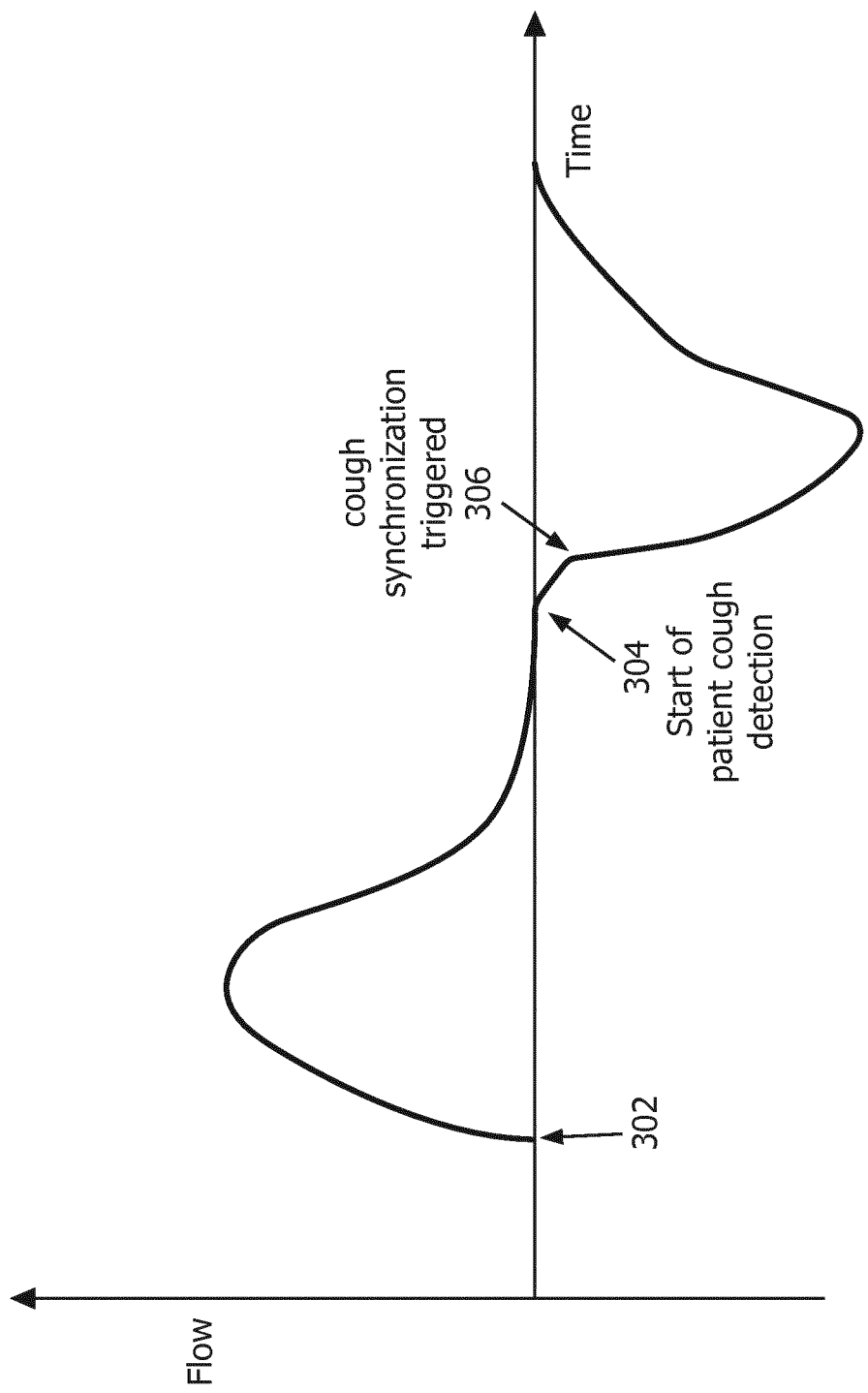
FIG. 3 illustrates an exemplary embodiment of cough synchronization based on a flow waveform associated with breathable gas in the subject interface communicated to the airway of a subject.

FIG. 3 illustrates an exemplary embodiment of cough synchronization based on a flow waveform associated with breathable gas in the subject interface communicated to the airway of a subject. As illustrated in FIG. 3, the flow rate slowly decreases to near zero at the end of the insufflation cycle. If a rapid decrease is observed at the end of the insufflation cycle at time 304, which may indicate an outflow being generated in subject interface 16, patient cough detection automatically starts. When the magnitude of the flow rate decreasing exceeds a flow rate threshold at time 306, cough synchronization is triggered and pressure generator 14 automatically switches to the exsufflation cycle to assist with the patient's cough.

Figure 4:
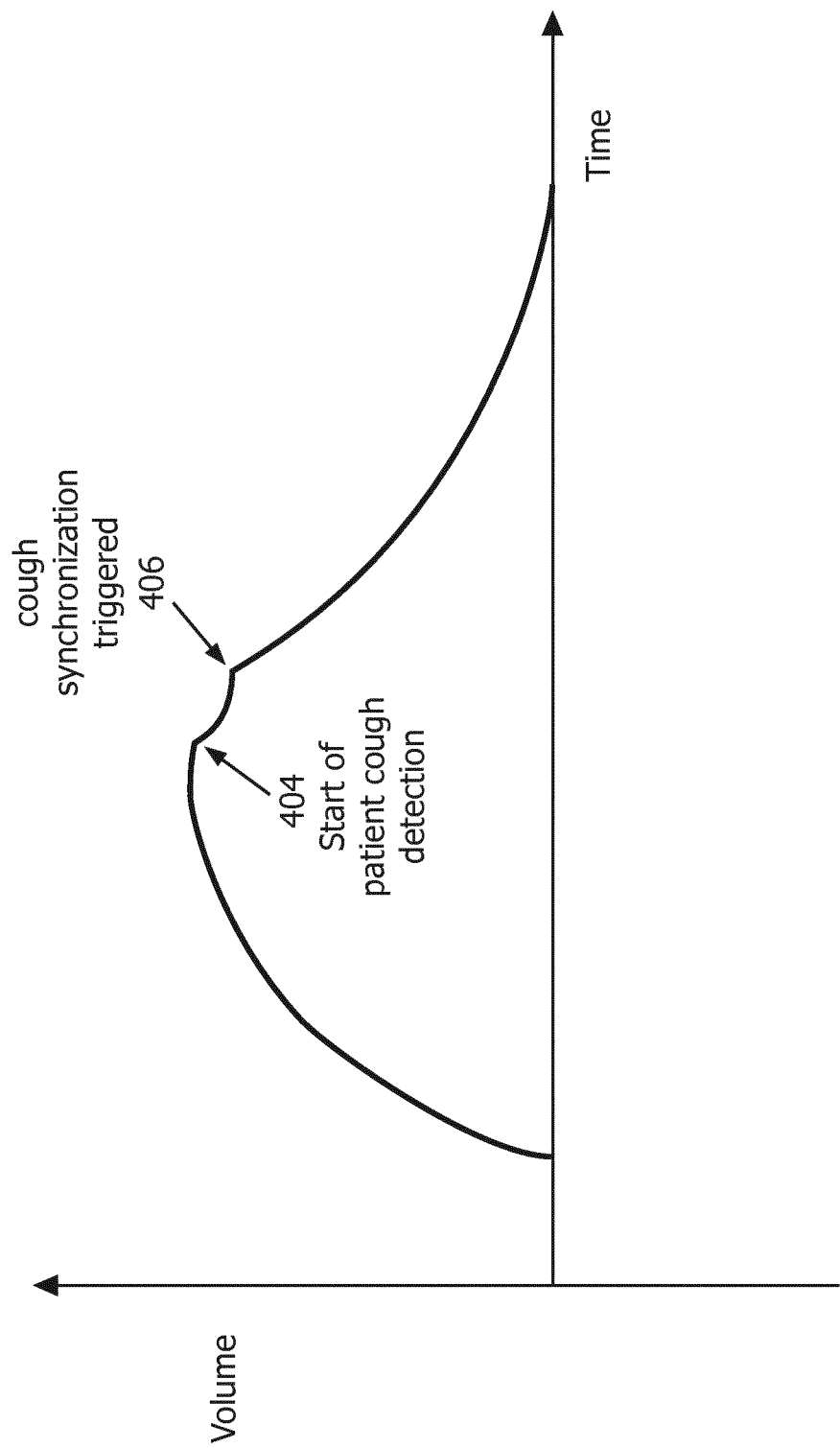
FIG. 4 illustrates an exemplary embodiment of cough synchronization based on a volume waveform associated with breathable gas in the subject interface communicated to the airway of a subject.

FIG. 4 illustrates an exemplary embodiment of cough synchronization based on a volume waveform associated with breathable gas in the subject interface communicated to the airway of a subject. As illustrated in FIG. 4, a total volume level associated with the gas in subject interface 16 approaches maximum at the end of the insufflation cycle. If a volume level drop is observed at the end of the insufflation cycle at time 404, which may indicate an effort to cough is made by the subject, the cough detection automatically starts. When the volume level drops to be less than a volume level threshold at time 406, cough synchronization is triggered and pressure generator 14 automatically switches to the exsufflation cycle to assist with the patient's cough.

Figure 5:
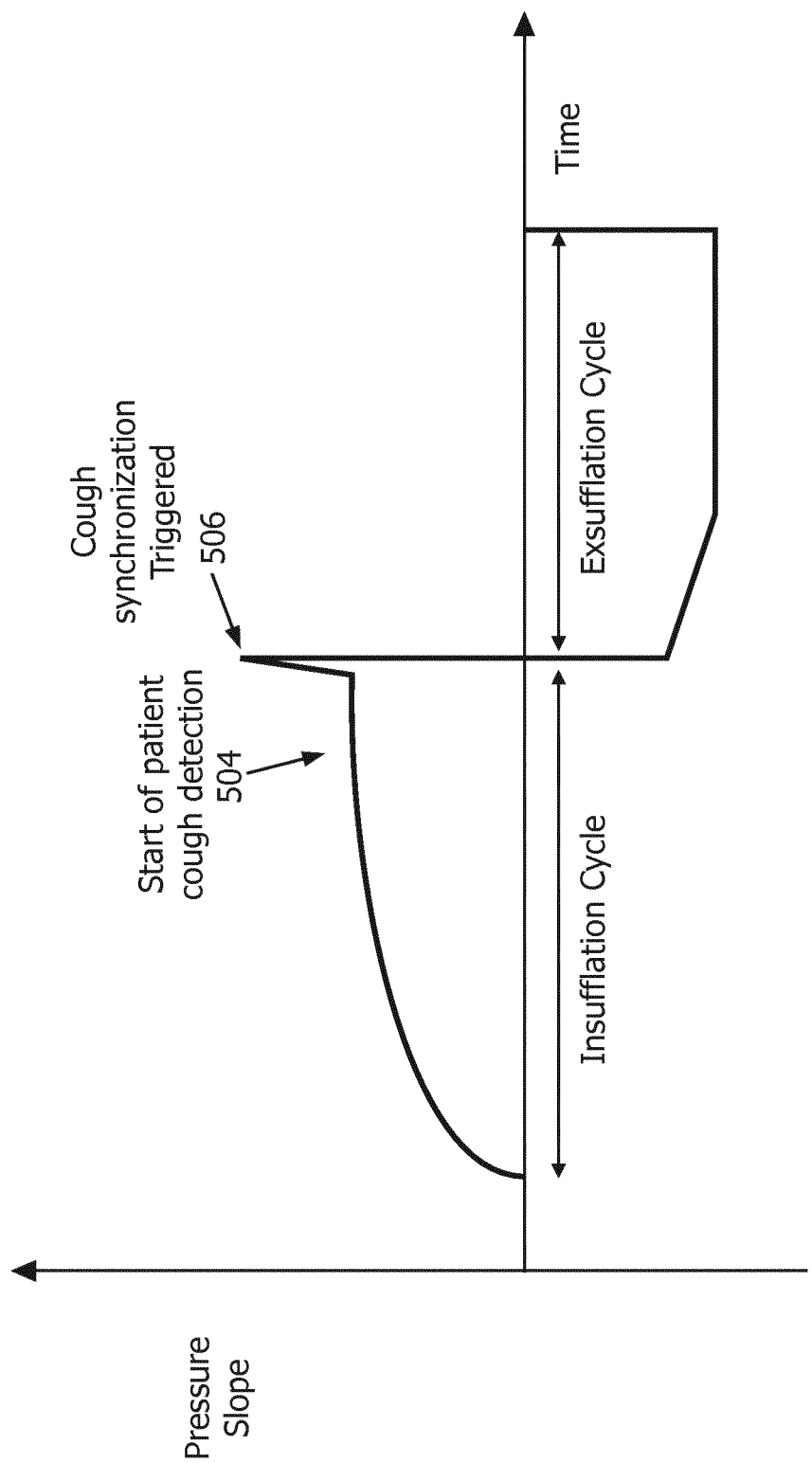
FIG. 5 illustrates an exemplary embodiment of cough synchronization based on a pressure waveform slope associated with breathable gas in the subject interface communicated to the airway of a subject.

FIG. 5 illustrates an exemplary embodiment of cough synchronization based on a pressure waveform slope associated with breathable gas in the subject interface communicated to the airway of a subject. As illustrated in FIG. 5, patient cough detection starts at time 504 when an increase in the pressure level is observed. System 10 measures the velocity of the pressure level increase continuously. Once the velocity of the pressure level exceeds a pressure waveform slope threshold at time 506, cough synchronization is automatically triggered, and the exsufflation cycle is started.

Figure 6:
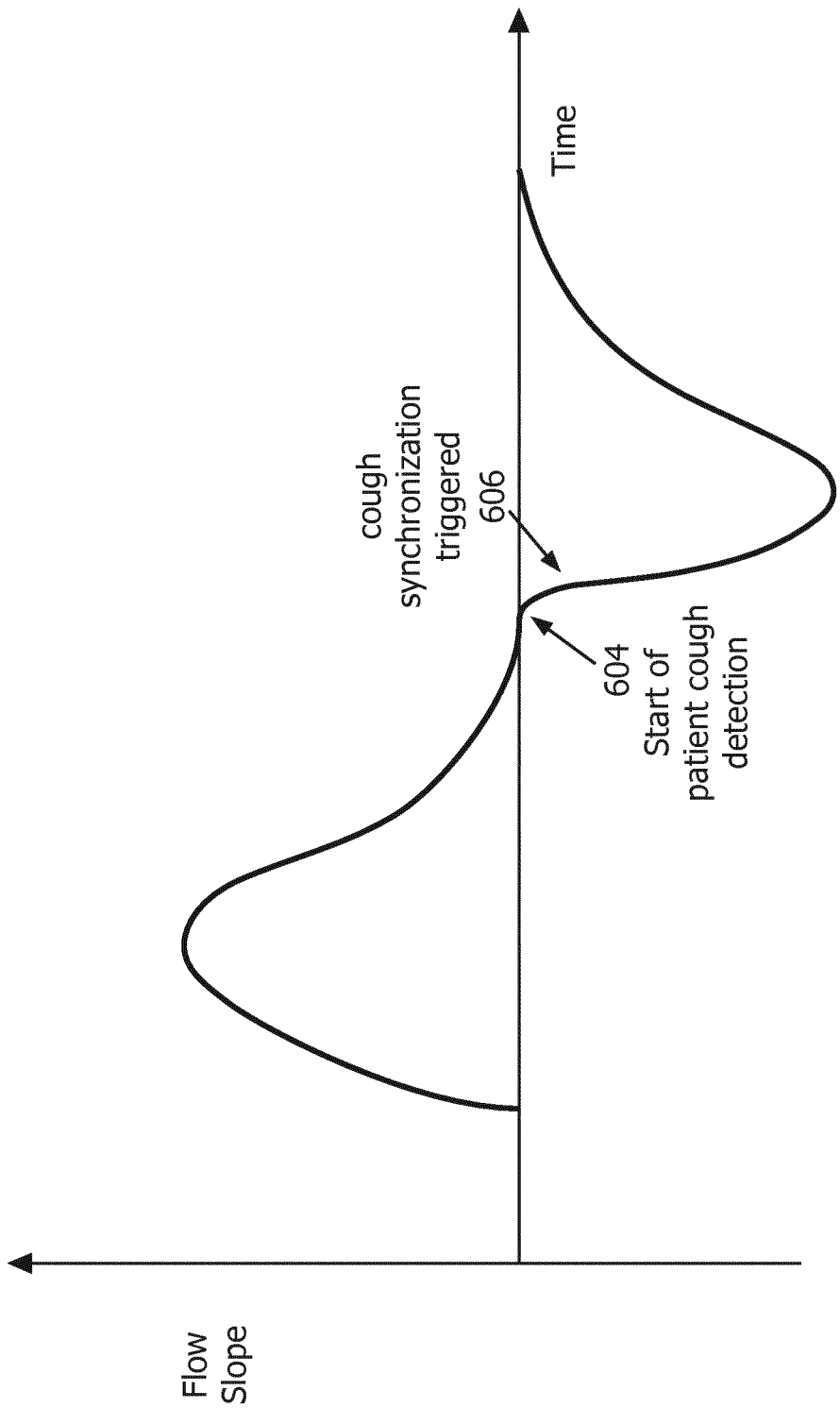
FIG. 6 illustrates an exemplary embodiment of cough synchronization based on a flow waveform slope associated with breathable gas in the subject interface communicated to the airway of a subject.

FIG. 6 illustrates an exemplary embodiment of cough synchronization based on a flow waveform slope associated with breathable gas in the subject interface communicated to the airway of a subject. As illustrated in FIG. 6, patient cough detection starts at time 604 when a decrease in the flow rate is observed. System 10 measures the velocity of the flow rate decrease. Once the velocity of the flow rate exceeds a flow waveform slope threshold at time 506, cough synchronization is automatically triggered.

Figure 7:
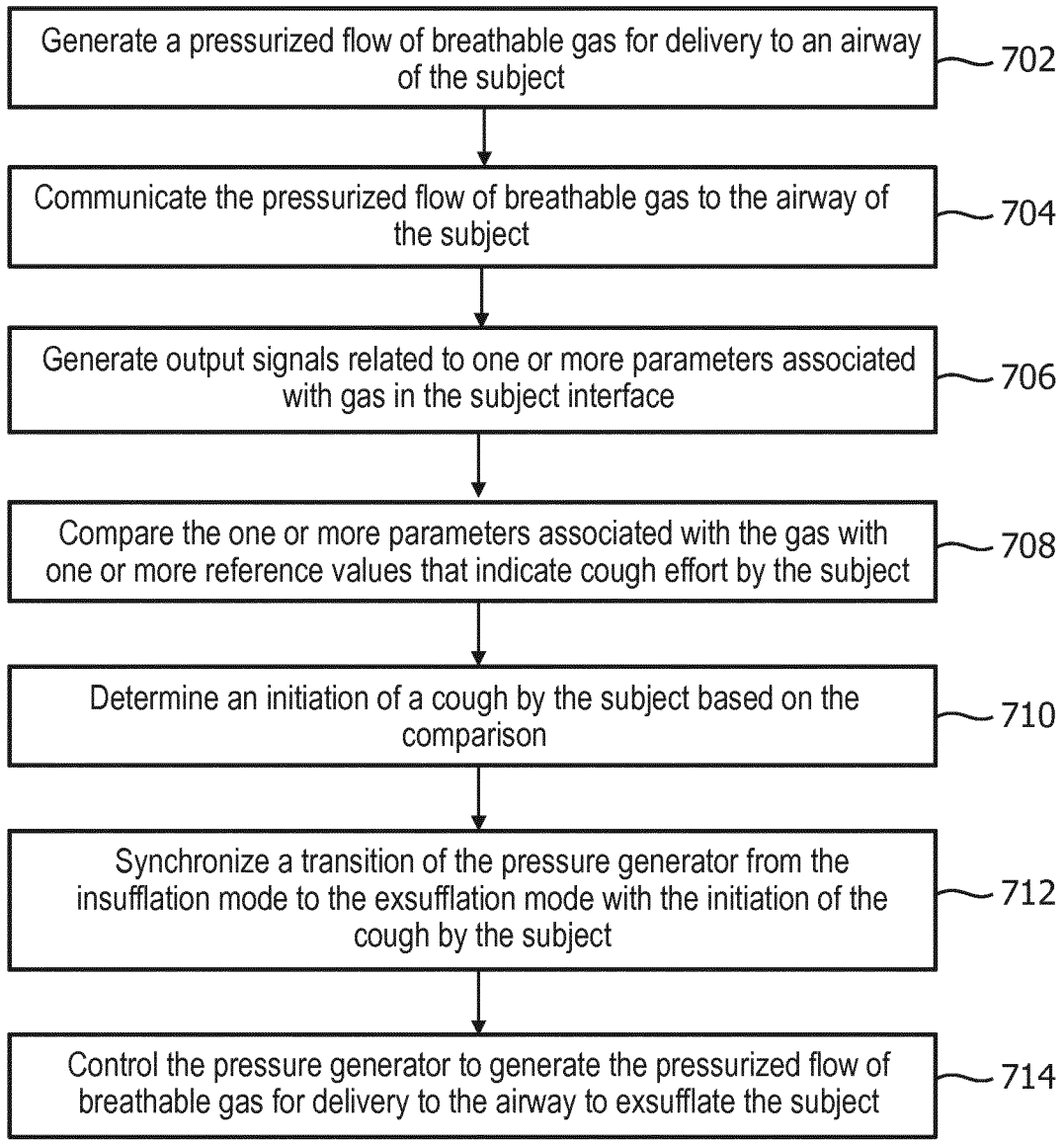
FIG. 7 illustrates an exemplary flowchart of the process for cough synchronization.

FIG. 7 illustrates an exemplary flowchart of the process for cough synchronization implemented on system 10. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 7 and described below is not intended to be limiting.

At operation 702, a pressurized flow of breathable gas is generated for delivery to an airway of the subject. In some embodiments, operation 702 is performed by a pressure generator the same as or similar to pressure generator 14 (shown in FIG. 1 and described herein).

At operation 704, the pressurized flow of breathable gas is communicated to the airway of the subject. In some embodiments, operation 704 is performed by a subject interface the same as or similar to subject interface 16 (shown in FIG. 1 and described herein).

At operation 706, output signals related to one or more parameters associated with gas in the subject interface is generated. In some embodiments, operation 706 is performed by sensors the same as or similar to sensors 18 (shown in FIG. 1 and described herein).

At operation 708, the one or more parameters associated with gas in the subject interface is compared with one or more reference values that indicate cough effort by the subject. In some embodiments, operation 708 is performed by a parameter analysis component the same as or similar to parameter analysis component 42 (shown in FIG. 1 and described herein).

At operation 710, an initiation of a cough by the subject is determined based on the comparison. In some embodiments, operation 710 is performed by a decision component the same as or similar to decision component 50 (shown in FIG. 1 and described herein).

At operation 712, a transition of the pressure generator from the insufflation mode to the exsufflation mode is synchronized with the initiation of the cough by the subject. In some embodiments, operation 712 is performed by a synchronization component the same as or similar to synchronization component 52 (shown in FIG. 1 and described herein).

At operation 714, the pressure generator is controlled to generate the pressurized flow of breathable gas for delivery to the airway to exsufflate the subject. In some embodiments, operation 714 is performed by a control component the same as or similar to control component 40 (shown in FIG. 1 and described herein).

Figure 8:
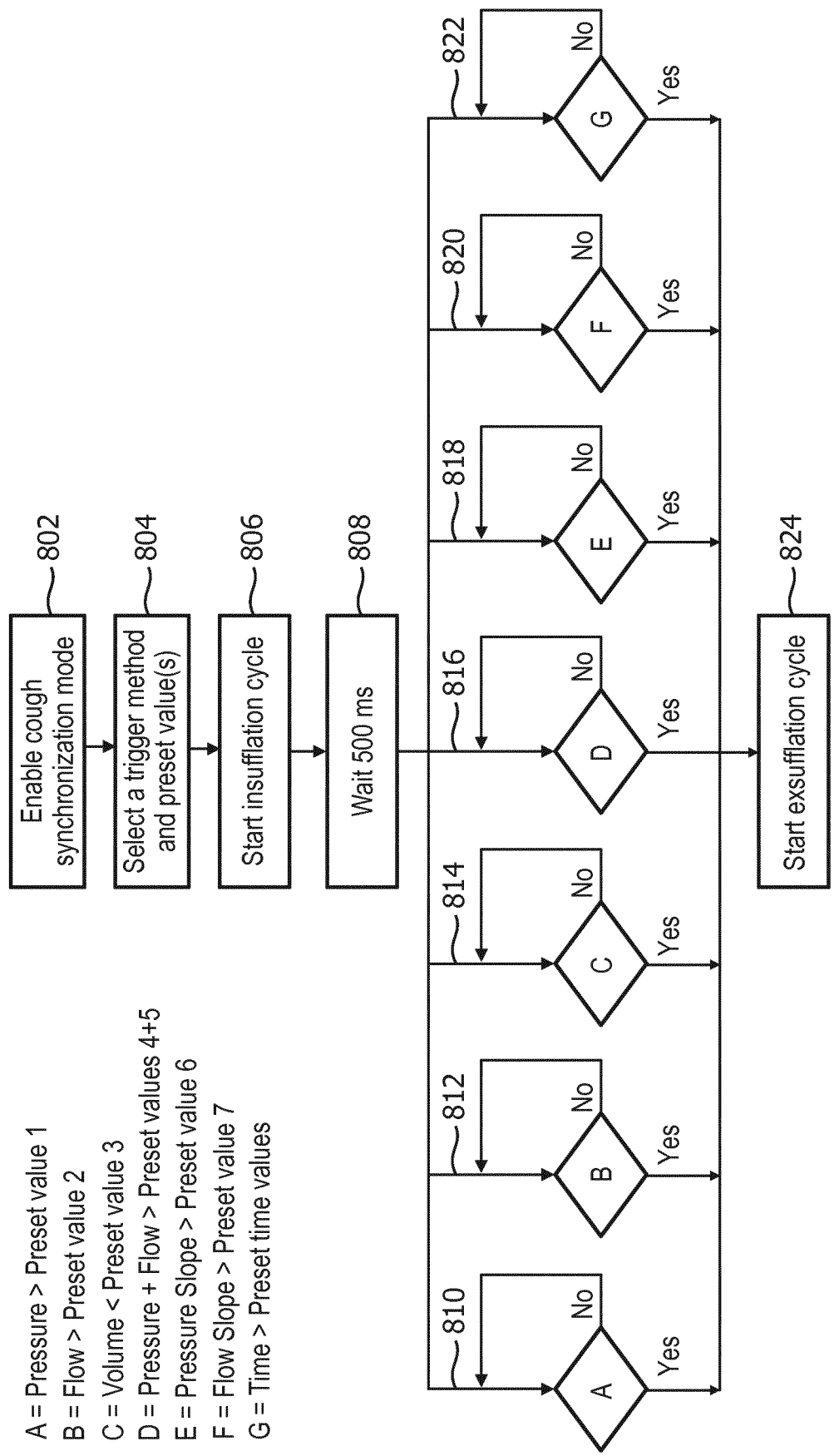
FIG. 8 illustrates another exemplary flowchart of the process for cough synchronization.

FIG. 8 illustrates another exemplary flowchart of the process for cough synchronization. It should be appreciated that the operations of the illustrated process presented below are intended to be illustrative. In some embodiments, the process may be accomplished with one or more additional operations not described, and/or without one or more of the operations discussed. Additionally, the order in which the operations of the process as illustrated in FIG. 8 and described below is not intended to be limiting.

At operation 802, a cough synchronization mode is enabled. In some embodiments, operation 802 is performed in accordance with input received at user interface the same as or similar to user interface 22 (shown in FIG. 1 and described herein), and processed by a control component the same as or similar to control component 40 (shown in FIG. 1 and described herein).

At operation 804, a trigger method and one or more preset values are selected. In some embodiments, operation 804 is performed in accordance with input received at user interface the same as or similar to user interface 22 (shown in FIG. 1 and described herein), and processed by a control component the same as or similar to control component 40 (shown in FIG. 1 and described herein).

At operation 806, the insufflation cycle starts. In some embodiments, operation 806 is performed by a pressure generator the same as or similar to pressure generator 14 (shown in FIG. 1 and described herein).

At operation 808, a time interval of 500 milliseconds is imposed at the end of the insufflation cycle to prevent false triggering of cough synchronization. In some embodiments, operation 808 is performed by a control component the same as or similar to control component 40 (shown in FIG. 1 and described herein).

At operation 810, a decision whether a cough is initiated by a subject is made based on the comparison of a pressure level associated with the gas in a subject interface with a preset pressure level value. In some embodiments, operation 810 is performed by a pressure analysis component the same as or similar to pressure analysis component 46 (shown in FIG. 1 and described herein).

At operation 812, a decision whether a cough is initiated by a subject is made based on the comparison of a flow rate associated with the gas in a subject interface with a preset flow rate value. In some embodiments, operation 812 is performed by a flow analysis component the same as or similar to flow analysis component 44 (shown in FIG. 1 and described herein).

At operation 814, a decision whether a cough is initiated by a subject is made based on the comparison of a volume level associated with the gas in a subject interface with a preset volume level value. In some embodiments, operation 814 is performed by a volume analysis component the same as or similar to volume analysis component 48 (shown in FIG. 1 and described herein).

At operation 816, a decision whether a cough is initiated by a subject is made based on the comparison of a pressure level associated with the gas in a subject interface with a preset pressure level value and the comparison of a flow rate associated with the gas in a subject interface with a preset flow rate value. In some embodiments, operation 816 is performed by a pressure analysis component the same as or similar to pressure analysis component 46, and a flow analysis component the same as or similar to flow analysis component 44 (shown in FIG. 1 and described herein).

At operation 818, a decision whether a cough is initiated by a subject is made based on the comparison of a pressure waveform slope associated with the gas in a subject interface with a preset pressure waveform slope value. In some embodiments, operation 810 is performed by a pressure analysis component the same as or similar to pressure analysis component 46 (shown in FIG. 1 and described herein).

At operation 820, a decision whether a cough is initiated by a subject is made based on the comparison of a flow rate slope associated with the gas in a subject interface with a preset flow slope value. In some embodiments, operation 812 is performed by a flow analysis component the same as or similar to flow analysis component 44 (shown in FIG. 1 and described herein).

At operation 822, a decision whether a cough is initiated by a subject is made based on whether a change observed in measurements related to one or more parameters associated with the gas in a subject interface continues to exceed a preset time value. In some embodiments, operation 822 is performed by one or more of a flow analysis component, a pressure analysis component and a volume analysis component, which are the same as or similar to flow analysis component 44, pressure analysis component 46 and volume analysis component 48, respectively (shown in FIG. 1 and described herein).

At operation 824, the insufflation cycle starts. In some embodiments, operation 806 is performed by a pressure generator the same as or similar to pressure generator 14 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the scope of the appended claims. For example, it is to be understood that the present disclosure contemplates that, to the extent possible, one or more features of any embodiment can be combined with one or more features of any other embodiment.

The invention claimed is:

1. A mechanical insufflation-exsufflation system, the system comprising:
   a pressure generator configured to operate in:
      an insufflation mode, wherein the pressure generator generates a positive pressurized flow of breathable gas for delivery to an airway of a subject via a subject interface, and
      an exsufflation mode, wherein the pressure generator generates a negative pressurized flow of breathable gas to draw gas from the airway of the subject via the subject interface;
   one or more sensors configured to generate output signals related to one or more parameters associated with gas in the system; and
   one or more processors operatively connected to the one or more sensors to receive the output signals and configured to:
      during the insufflation mode, determine an initiation of a cough by the subject based on one or more of:
         a decrease of a flow rate associated with the breathable gas in the subject interface,
         an increase of a pressure level associated with the breathable gas in the subject interface,
         an increase of a pressure waveform slope associated with the breathable gas in the subject interface in comparison with a preset pressure waveform slope value, and/or
         a decrease of a flow rate slope associated with the breathable gas in the subject interface in comparison with a preset flow slope value;
      synchronize a transition of the pressure generator from the insufflation mode to the exsufflation mode with the initiation of the cough by the subject without manual configuration; and
      control generation and delivery of the pressurized flow of breathable gas to the airway of the subject in the exsufflation mode to exsufflate the subject.

2. The system of claim 1, wherein the one or more processors operatively connected to the one or more sensors to receive the output signals are configured to determine the initiation of the cough by the subject based on the decrease of the flow rate associated with the breathable gas in the subject interface.

3. The system of claim 2, wherein the decrease of the flow rate associated with the breathable gas in the subject interface is an abrupt decrease.

4. The system of claim 1, wherein the one or more processors operatively connected to the one or more sensors to receive the output signals are configured to determine the initiation of the cough by the subject based on the increase of the pressure level associated with the breathable gas in the subject interface.

5. The system of claim 4, wherein the increase of the pressure level associated with the breathable gas in the subject interface is an abrupt increase.

6. The system of claim 1, wherein the one or more processors operatively connected to the one or more sensors to receive the output signals are configured to determine the initiation of the cough by the subject based on the increase of the pressure waveform slope associated with the breathable gas in the subject interface in comparison with the preset pressure waveform slope value.

7. The system of claim 1, wherein the one or more processors operatively connected to the one or more sensors to receive the output signals are configured to determine the initiation of the cough by the subject based on the decrease of the flow rate slope associated with the breathable gas in the subject interface in comparison with the preset flow slope value.

8. A method of cough synchronization in a mechanical insufflation-exsufflation system, the method comprising:
   generating a pressurized flow of breathable gas for delivery to an airway of the subject in an insufflation mode and an exsufflation mode;
   during the insufflation mode, determining an initiation of a cough by the subject based on one or more of:
      a decrease of a flow rate associated with the breathable gas in the subject interface,
      an increase of a pressure level associated with the breathable gas in the subject interface,
      an increase of a pressure waveform slope associated with the breathable gas in the subject interface in comparison with a preset pressure waveform slope value, and/or
      a decrease of a flow rate slope associated with the breathable gas in the subject interface in comparison with a preset flow slope value; and
   synchronizing a transition of the pressure generation from the insufflation mode to the exsufflation mode with the initiation of the cough by the subject.

9. The method of claim 8, wherein the initiation of the cough by the subject is determined based on the decrease of the flow rate associated with the breathable gas in the subject interface.

10. The method of claim 9, wherein the decrease of the flow rate associated with the breathable gas in the subject interface is an abrupt decrease.

11. The method of claim 8, wherein the initiation of the cough by the subject is determined based on the increase of the pressure level associated with the breathable gas in the subject interface.

12. The method claim 11, wherein the increase of the pressure level associated with the breathable gas in the subject interface is an abrupt increase.

13. The method of claim 8, wherein the initiation of the cough by the subject is determined based on the increase of the pressure waveform slope associated with the breathable gas in the subject interface in comparison with the preset pressure waveform slope value.

14. The method of claim 8, wherein the initiation of the cough by the subject is determined based on the decrease of the flow rate slope associated with the breathable gas in the subject interface in comparison with the preset flow slope value.

* * * * *